United States Patent
Campian et al.

(10) Patent No.: US 6,600,016 B1
(45) Date of Patent: Jul. 29, 2003

(54) MULTIFUNCTIONALIZED SOLID SUPPORT RESINS FOR SYNTHESIS OF COMBINATORIAL LIBRARIES AND METHOD FOR USING THE SAME

(75) Inventors: Eugene Campian, Louisville, KY (US); Boliang Lu, Louisville, KY (US); Jinfang Zhang, Louisville, KY (US)

(73) Assignee: Advanced Syntech LLC, Louisville, KY (US)

( * ) Notice: Subject to any disclaimer, the term of this patent is extended or adjusted under 35 U.S.C. 154(b) by 0 days.

(21) Appl. No.: 09/379,848

(22) Filed: Aug. 24, 1999

(51) Int. Cl.$^7$ ................................................. C07K 1/04
(52) U.S. Cl. ...................... 530/334; 530/333; 530/335; 530/336; 530/337
(58) Field of Search ................................ 530/333, 334, 530/335–337

(56) References Cited

U.S. PATENT DOCUMENTS

| | | | | |
|---|---|---|---|---|
| 4,156,618 A | * | 5/1979 | Iwami | 127/46 A |
| 4,205,134 A | * | 5/1980 | Seita | 521/53 |
| 4,396,051 A | * | 8/1983 | Ogawa | 151/203 |
| 4,533,562 A | * | 8/1985 | Ikegami | 427/3 |
| 5,457,080 A | * | 10/1995 | Takano | 503/207 |
| 5,597,894 A | * | 1/1997 | Coy | 530/311 |
| 5,977,076 A | * | 11/1999 | Anderson | 514/19 |
| 6,015,645 A | * | 1/2000 | Murti | 430/59 |
| 6,020,119 A | * | 2/2000 | Foucher | 430/627 |
| 6,028,147 A | * | 2/2000 | Ogawa | 525/292 |

* cited by examiner

*Primary Examiner*—Christopher S. F. Low
*Assistant Examiner*—David Lukton
(74) *Attorney, Agent, or Firm*—Stites & Harbison PLLC; John E. Vanderburgh

(57) ABSTRACT

Multifunctionalized support resin for the solid phase synthesis of combinatorial libraries is disclosed. The support resin comprises a resin backbone to which is attached a template containing at least two more attachment points which carry mutiple functionalized benzyl-type linkers. Each linker displays differing chemical stability under cleavage conditions so that products can be selectively and sequentially cleaved and separated from the reaction vessel. The linkers are independently different benzyl-type moieties, and each product synthesized on the linkers may have a different chemical structure. The support resin may further comprise an additional linker which is directly attached to the resin backbone. This linker can benzyl-type linkers or other traditional cleavable-linkers. The invention is further directed to a method for the production of mutiple combinatorial libraries in a simultaneous fashion utilizing the above described support resin. The products are selectively cleaved under conditions where only one linker site is cleaved so that the product is individually separated from the reaction vessel.

13 Claims, 11 Drawing Sheets

1

2

3

4

5

6

7

8

MULTIFUNCTIONALIZED SOLID SUPPORT RESINS FOR SYNTHESIS OF COMBINATORIAL LIBRARIES AND METHOD FOR USING THE SAME

FIELD OF THE INVENTION

The present invention relates to high-speed parallel synthesis of combinatorial libraries and more particularly to a multifunctionalized solid support resin and to a method for the synthesis of combinatorial libraries using a multifunctional solid support resin.

BACKGROUND OF THE INVENTION

The use of solid phase synthesis techniques for the synthesis of polypeptides and oligonucleotides are well known in the art. More recently, the use of solid phase techniques for the synthesis of small organic molecules has become a major focus of research. Of prime importance has been the ability of solid phase techniques to be automated, with an attendant increase in compound throughput and efficiency in research. This has been exploited with great vigor in the area of pharmaceutical research where it has been estimated that 10,000 compounds must be synthesized and tested in order to find one new drug (Science, 259, 1564, 1993). The focus on combinatorial chemistry techniques to increase compound throughput has now become almost universal in the pharmaceutical and agricultural industries.

An additional aspect relates to the chemical diversity of the compound stocks that are available for screening in pharmaceutical companies in the search for new lead structures. These have tended to be limited to the classes of compounds previously investigated through medicinal chemical techniques within each company. Therefore the availability of new classes of molecules for screening has become a major need.

Combinatorial chemistry involves both the synthesis and screening of large sets of compounds, called libraries. The libraries themselves can be arrays of individual compounds or mixtures. Therefore, the synthetic approaches are also classified into two categories, including combinatorial synthesis of mixtures and parallel synthesis leading to individual compounds. For screening purposes it is also important that the formed compounds be synthesized in 1 to 1 molar ratios.

In the first approach to creating molecular diversity, the combinatorial synthesis comprises multiple reactions in one reaction vessel resulting in the generation of all possible product combinations from a set of reactants. The simplest manifestation of the approach is to allow several reagents to react in solution at the same time to form all possible products. Among the examples is the synthesis of a library of over 97,000 members by reaction of a mixture of amines with 9,9-dimethylxanthene-2,4,5,7-tetracarboxylic acid tetrachloride (Carell, T; et al. Angew. Chem. Int. Ed. Engl. 33, 2059). However, this approach is usually unproductive unless the reagents are few and their reactivities are well matched to approach formation of the various compounds in 1 to 1 mol ratios.

Another approach is the use of the portioning-mixing method or the split synthesis (Furka, A; et al. Int. J. Pept. Protein Res. 37, 487, 1991). The synthesis is executed by repetition of three simple operations, including dividing a monofunctional solid support resin into equal portions, reacting each portion individually with one of the building blocks and then homogeneously mixing the portions. Starting with a single substance the number of compounds is tripled after each coupling step. For example, in the preparation of trimers, 27 different compounds can be prepared in three pools. These compounds can be cleaved into solution and screened as soluble pools, or the ligands can remain attached to the beads and screened in immobilized form. However, biological screens performed on such large mixtures of soluble compounds can be ambiguous since the observed activity could be due to a single compound or to a combination of compounds acting either collectively or synergistically. The subsequent identification of specific biologically active members is challenging, since the numbers of compounds present in the pools and their often limited concentration deter their isolation and re-assay. Because of this, the identification of individual active compounds from the library requires the repetitive re-synthesis and re-testing of the most active smaller subsets of the library until activity data are obtained on homogenous compounds. There is no direct method available to elucidate the chemical structures of large libraries of mixtures. However many methods have been developed to aid and accelerate the deconvolution process, including recursive deconvolution and multiple encoding approaches. There still remain a number of critical issues in screening libraries consisting of large mixtures of compounds.

By contrast, many other practitioners are using a method called parallel, or robotic, synthesis. This practice simply involves performing a series of individual reactions in separate vessels. Using traditional manual organic synthesis a chemist can synthesize only about 50 compounds per year. By the use of robots, which can perform multiple reactions simultaneously, this procedure can be made more efficient.

One of earliest examples of the parallel method for the synthesis of compounds is the multi-pin method developed by Geysen et al., for combinatorial solid-phase peptide synthesis (Geysen et al.; J. Immunol. Meth. (1987) 102:259–274). According to this method, a series of 96 pins are mounted on a block in an arrangement and spacing which correspond to a 96-well microtiter reaction plate, and the surface of each pin is derivatized to contain terminal linker functional groups. The pin block is then lowered into a series of reaction plates to immerse the pins in the wells of the plates where coupling occurs at the terminal linker functional groups, and a plurality of further reactions are carried out in a similar fashion. Reagents varying in their substituent groups occupy the wells of each plate in a predetermined array, to form a unique product on each pin. By using different combinations of substituents, one achieves a large number of different compounds with an array of central core structures.

Another type of solid phase parallel synthesis method is the diversomer approach from Park-Davis group (DeWitt, S. H.; et al. Proc. Natl. Acad. Sci. USA, 90, 6909, 1993). It was designed for the synthesis of small organic molecules. The solid support resin was placed into porous tubes immersed into tubes containing the various reagents which pass through the porous walls to contact the solid phase support resin.

A related method of synthesis uses porous polyethylene bags (Tea Bag method) containing the functionalized solid phase resins (Houghton, R. A., et al., Nature, 354, 84–86, 1991). These bags of resin can be moved from one reaction vessel to another in order to undergo a series of reaction steps for the synthesis of libraries of products.

As a consequence of the development of the efficient automation equipment and processes, the parallel synthesis technique has now become the most extensively used method in combinatorial chemistry. However, the libraries created using the parallel method (one compound per vessel) usually require more steps than those created using other combinatorial syntheses. As a result, more time is required to synthesize a comparable size library than would be required using other combinatorial techniques, such as the portioning-mixing method discussed above.

In view of the above, the field of pharmaceutical and agricultural research has a strong need for highly flexible technologies to generate a large number of novel classes of compounds for screening and clinical testing.

Solid Support Resins:

Solid support resin synthesis is carried out on a substrate consisting of a polymer, cross-linked polymer, functionalized polymeric pin, or other insoluble material. These polymers or insoluble materials have been described in literature and are known to those who are skilled in the art of solid phase synthesis (Stewart J M, Young J. D.; Solid Phase Peptide Synthesis, 2nd Ed; Pierce Chemical Company: Rockford. Ill., 1984). Some of them are based on polymeric organic substrates such as polyethylene, polystyrene, polypropylene, polyethylene glycol, polyacrylamide, and cellulose. Additional types of supports include composite structures such as grafted copolymers and polymeric substrates such as polyacrylamide supported within an inorganic matrix such as kieselguhr particles, silica gel, and controlled pore glass.

Examples of suitable support resins and linkers are given in various reviews (Barany, G.; Merrifield, R. B. "Solid Phase Peptide Synthesis ", in "The Peptides—Analysis, Synthesis, Biology". Vol 2, [Gross, E. and Meienhofer, J., Eds.], Academic Press, Inc., New York, 1979, pp 1–284; Backes, B. J.; Ellman, J. A. Curr. Opin. Chem. Biol. 1997. 1, 86; James, I. W., Tetrahedron 1999, 55, 4855–4946) and in commercial catalogs (Advanced ChemTech, Louisville, Ky.; Novabiochem, San Diego, Calif.). Some examples of particularly useful functionalized resin/linker combinations that are meant to be illustrative and not limiting in scope are shown below:

Aminomethyl Polystyrene Resin (Mitchell, A. R., et al., J. Org. Chem., 1978, 43, 2845):

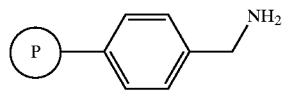

This resin is the core of a wide variety of synthesis resins. The amide linkage can be formed through the coupling of a carboxylic acid to amino group on solid support resin under standard peptide coupling conditions. The amide bond is usually stable under the cleavage conditions for most acid labile, photo labile and base labile or nucleophilic linkers.

Acid Labile Resins:

1. Wang resin (Wang, S. S.; J. Am. Chem. Soc. 1973, 95, 1328–1333).

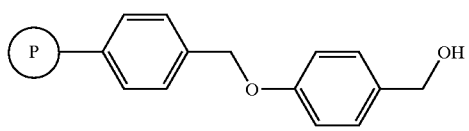

Wang resin is perhaps the most widely used of all resins for acid substrates bound to the solid support resin. The linkage between the substrate and the polystyrene core is through a 4-hydroxybenzyl alcohol moiety. The linker is bound to the resin through a phenyl ether linkage and the carboxylic acid substrate is usually bound to the linker through a benzyl ester linkage. The ester linkage has good stability to a variety of reaction conditions, but can be readily cleaved under acidic conditions, such as by using 25% TFA in DCM.

2. Rink resin (Rink, H.; Tetrahedron Lett. 1987, 28, 3787).

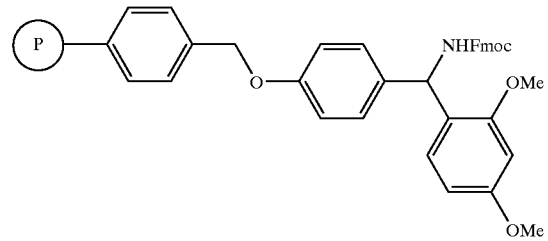

Rink resin is used to prepare amides utilizing the Fmoc strategy. It has also found tremendous utility for a wide range of solid phase organic synthesis protocols. The substrate is assembled under basic or neutral conditions, then the product is cleaved under acidic conditions, such as 10% TFA in DCM.

3. Knorr resin (Bernatowicz, M. S., et al. Tetrahedron lett., 1989, 30, 4645).

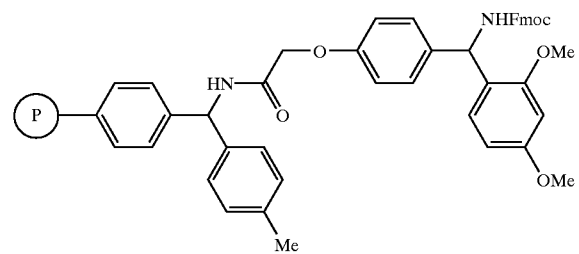

Knorr resin is very similar to Rink resin, except that the linker has been modified to be more stable to TFA. Typically, the product is cleaved from the Knorr resin using 95% TFA in DCM.

4. PAL resin (Bernatowicz, M. S., et al. Tetrahedron lett., 1989, 30, 4645).

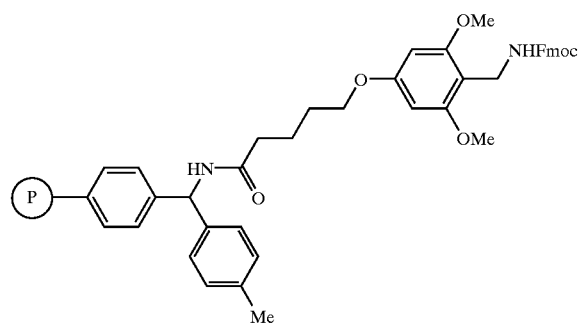

PAL resin is an acid labile resin developed for the synthesis of amides by Fmoc chemistry. Like Rink and Knorr resins, products are cleaved from PAL resin in the presence of TFA. However, compared to Knorr resin, PAL resin is more than two times as active towards cleavage.

5. HMBA-MBHA Resin (Sheppard, R. C., et al., Int. J. Peptide Protein Res. 1982, 20, 451).

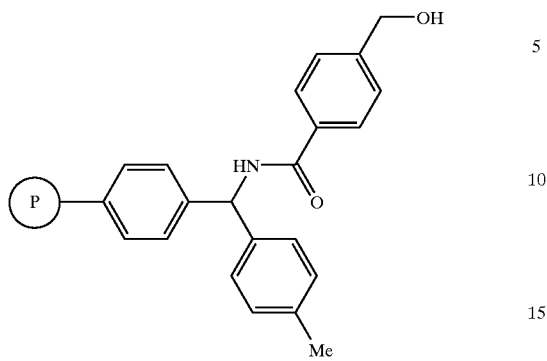

This resin has been widely used in solid phase organic synthesis and in peptide synthesis, especially in the synthesis of cyclic peptides, peptides containing C-terminal amino acid alcohols. The products can be cleaved from the resin using a variety of nucleophiles, such as hydroxides, amines or alkoxides to give carboxylic acids, amides and esters.

6. HMPA resin. This also is an acid labile resin which provides an alternative to Wang resin and represented as:

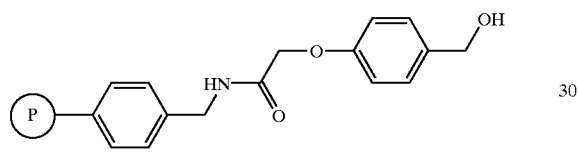

7. Benzhydrylamine copoly(styrene-1 or 2%-divinylbenzene) which referred to as the BRA resin (Pietta, P. G., et al., J. Org. Chem. 1974, 39, 44).

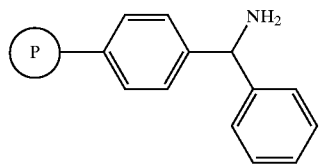

BHA resin is the first resin developed for preparing peptide C-terminal amides using Boc chemistry. The products can be cleaved under strong acidic conditions, such as using HF.

8. Methyl benzhydrylamine copoly(styrene-1 or 2%-divinylbenzene) which is referred to as MBHA and represented as:

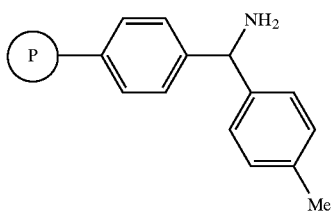

This resin can be cleaved more easily than benzhydrylamine resin. But strong acids are still required to effieciently cleave the products from the resin.

9. Trityl and functionalized Trityl resins, such as aminotrityl resin and amino-2-chlorotrityl resin (Barlos, K.; Gatos, D.; Papapholiu, G.; Schafer, W.; Wenqing, Y.; Tetrahedron Lett. 1989, 30, 3947). These are highly acid labile resin for the introduction of an amino group or for the synthesis of amides.

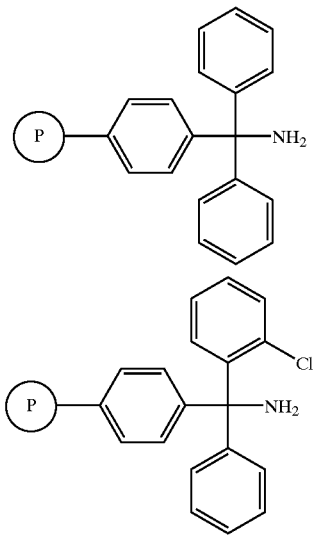

10. Sieber amide resin (Sieber, P.; Tetrahedron Lett. 1987, 28, 2107). This resin is useful for preparing amides and amines. Like Rink resin, products can be cleaved using TFA in DCM.

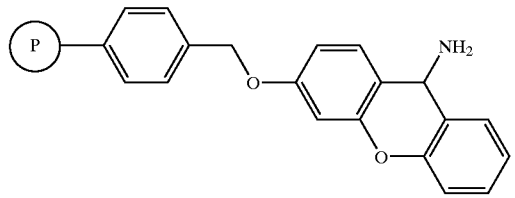

Because it is less sterically hindered than Rink resin, this resin allows for higher loading in more sterically demanding applications.

10. Rink acid resin (Rink, H., Tetrahedron Lett., 1987, 28, 3787).

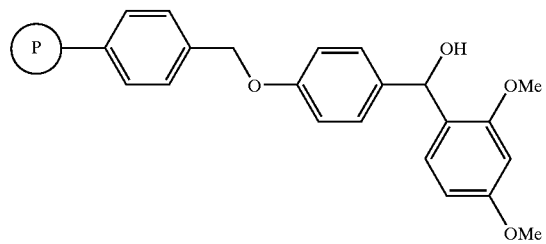

This resin can be cleaved under conditions as mild as 10% acetic acid. The nature of this resin is that the hydroxyl group can be considered weakly nucleophilic or electrophilic depending on the reaction conditions.

12. HMPB-BHA resin (4-hydroxymethyl-3-methoxyphenoxybutyric acid-BHA Florsheimer, A.; Riniker, B. in "Peptides 1990; Proceedings of the 21$^{st}$ European Peptide Symposium", [Giralt, E. and Andreu, D. Eds.], ESCOM, Leiden, 1991, pp 131.

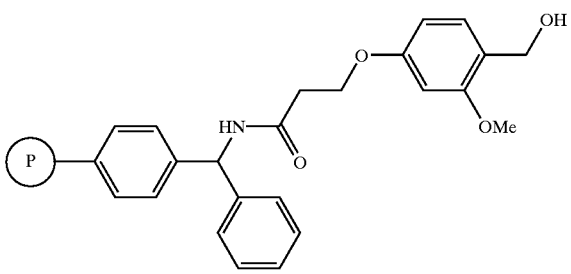

This is a super acid sensitive resin on which the carboxylic acids are released with 1% TFA in DCM.

Base Labile or Nucleophilic Resins:

1. Merrifield resin—Chloromethyl co-poly(styrene-1 or 2%-divinylbenzene) which can be represented as:

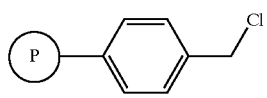

A carboxylic acid substrate is attached to the resin through nucleophilic replacement of chloride under basic conditions. The resin is usually stable under acidic conditions, but the products can be cleaved under basic and nucleophilic conditions in the presence of amine, alcohol, thiol and $H_2O$.

2. Hydroxymethyl polystyrene resin (Wang, S. S., J. Org. Chem., 1975, 40, 1235).

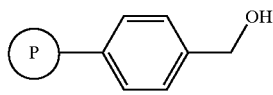

The resin is an alternative to the corresponding Merrifield resin, whereas the substrate is attached to a halomethylated resin through nucleophilic displacement of halogen on the resin, the attachment to hydroxymethylated resins is achieved by coupling of activated carboxylic acids to the hydroxy group on the resin or through Mitsunobu reactions. The products can be cleaved from the resin using a variety of nucleophiles, such as hydroxides, amines or alkoxides to give carboxylic acids, amides and esters.

3. Oxime resin (DeGrado, W. F.; Kaiser, E. T.; J.Org. Chem. 1982, 47, 3258).

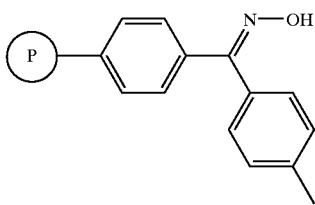

This resin is compatible to Boc chemistry. The product can be cleaved under basic conditions.

Photolabile Resins (e.g. Abraham, N. A. et al.; Tetrahedron Lett. 1991, 32, 577):

The products can be cleaved from these resins photolytically under neutral or mild conditions, making these resins useful for preparing pH sensitive compounds. Examples of the photolabile resins include 1. ANP resin:

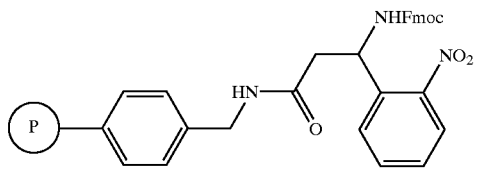

2. alpha-bromo-alpha-methylphenacyl polystyrene resin:

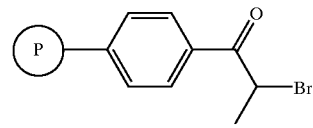

Safety Catch Resins (see resin reviews above; Backes, B. J.; Virgilio, A. A.; Eliman, J. Am. Chem. Soc. 1996, 118, 3055–6):

These resins are usually used in solid phase organic synthesis to prepare carboxylic acids and amides, which contain sulfonamide linkers stable to basic and nucleophilic reagents. Treating the resin with haloacetonitriles, diazomethane, or $TMSCHN_2$ activates the linkers to attack, releasing the attached carboxylic acid as a free acid, an amide or an ester depending on whether the nucleophile is a hydroxide, amine, or alcohol, resepectively. Examples of the safty catch reasins include:

20. 4-sulfamylbenzoyl-4'-methylbenzhydrylamine resin:

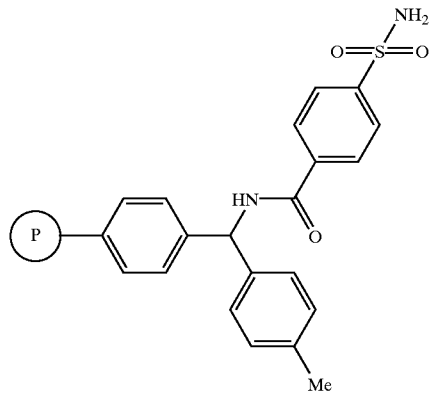

21. 4-sulfamylbutryl-4'-methylbenzhydrylamine resin:

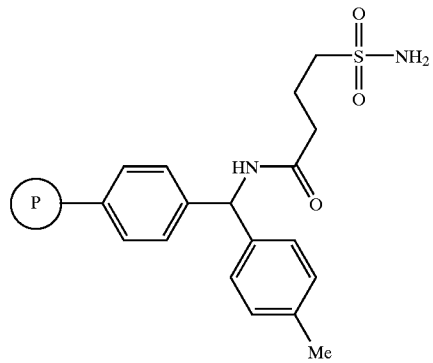

TentaGel Resins:

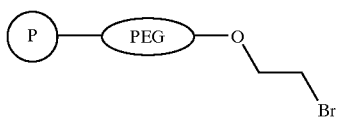

TentaGel resins are polyoxyethyleneglycol (PEG) grafted (Tentagel) resins (Rapp, W.; Zhang, L.; Habich, R.; Bayer, E. in "Peptides 1988; Proc. 20$^{rth}$ European Peptide Symposium" [Jung,G. and Bayer, E., Eds.], Walter de Gruyter, Berlin, 1989, pp 199–201. TentaGel resins, e.g. TentaGel S Br resin can swell in a wide variety of solvents and the bead size distribution is very narrow, making these resins ideal for solid phase organic synthesis of combinatorial libraies. TentaGel S Br resin can immobilize carboxylic acids by displacing the bromine with a carboxylic acid salt. The products can be released by saponification with dilute aqueous base. *Resins with silicon linkage* (Chenera, B.; Finkelstein, J. A.; Veber, D. F.; J. Am. Chem. Soc. 1995, 117, 11999–12000; Woolard, F. X.; Paetsch, J.; Ellman, J. A.; J. Org. Chem. 1997, 62, 6102–3). Some examples of these resins contain protiodetachable arylsilane linker and traceless silyl linker. The products can be released in the presence of fluoride.

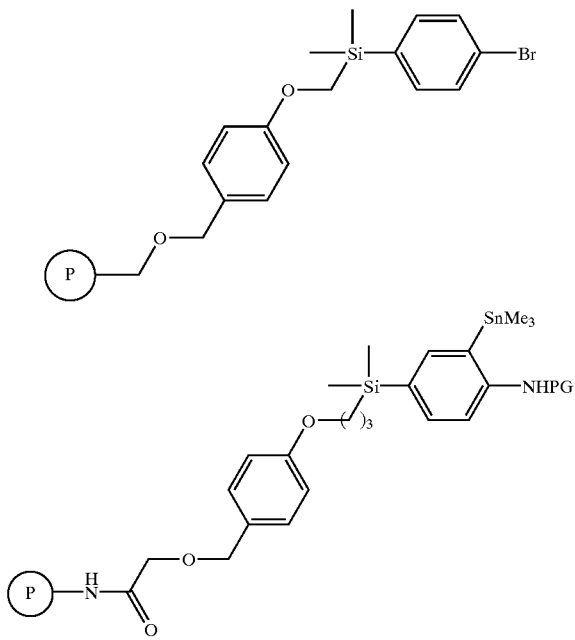

As described above, a wide variety of resins containing different linkers have been developed. The design of novel linkers suitable for the solid phase synthesis of small organic compounds has received great attention over the last few years. It is very clear that the quality of the combinatorial libraries synthesized on solid support resin, such as the range of yield and purity, depends not only on the synthetic strategy for the construction of the molecules but also on the nature of the resins and linkers to be chosen. The linkers can be divided into several classes based upon their stability, such as acid labile, base labile, photolabile, safety catch and traceless linkers. In conventional strategy for solid phase synthesis, the resin to be used contains the same linker so that the product is expected to be completely cleaved under an appropriate condition.

Recently, U.S. Pat. No. 5,635,598 disclosed selective cleavable linkers based on iminodiacetic acid ester and its application to solid phase peptide synthesis. The method is directed to cleavable linkers that can release peptide from the solid phase support resin under relatively mild conditions by formation of a diketopiperazine or other cyclic structure, such that the cyclic structure remains on the solid support resin, and, in a second cleavage, under more stringent conditions of high pH. This type of linker was claimed to be further combined with another cleavable linker which is also attached to the solid support resin backbone. The multiple linkers can then be cleaved selectively so that the desired peptide is sequentially released.

Another multiple release system based on a combination of benzyl ester type acid labile linkers with different sensitivities toward acid has been described (M. Cardno and M. Bradley, Tetrahedron lett., 37, 135, 1996. In this approach, three different linkers were coupled to the core resin, aminomethyl resin, in 1:1:1 molar ratio which was then applied to the peptide synthesis. The most acid labile linker releases the peptide product in 1% TFA, while the second linker needs 95% TFA. The third copy of the same peptide serves the purpose of analysis or on-bead assays. However, the synthesis of different products on these resins has not been reported yet.

A novel method based on the resin combination strategy was disclosed recently by us in a U.S. patent application Ser. No: 09/264,515 now abandoned. In this approach the multiple resins containing different linkers are combined in the same reaction vessel in which a plurality of chemical reactions are carried out to create multiple products on these solid supports respectively, which are then sequentially cleaved from the resins under the appropriate cleavage conditions. The method has been extensively used at Helios Pharmaceuticals in the synthesis of small organic combinatorial libraries.

SUMMARY OF THE INVENTION

Accordingly, it is an object of this invention to provide a single solid support resin that will provide for the production of a variety of different small organic compounds in a single reaction vessel.

Another object of this invention is to provide a flexible technology for high throughput parallel synthesis of combinatorial libraries.

Yet another object is to provide a method for efficiently forming combinatorial libraries in which the compounds are formed substantially in molar ratios of 1 to 1.

Yet another object of the invention is to provide a method for forming a variety of different compounds and for recovering the various compounds in a pure state without contamination by the other formed compounds.

The present invention is directed to multifunctionalized solid phase support resins for as the preparation of combinatorial libraries and to a method for high-speed parallel synthesis of combinatorial libraries utilizing multifuntionalized solid phase support resins. Such multifunctionalized support resins comprise polymers that contain a core template having multiple sites that can be attached by one or more linkers. The linkers incorporate reactive functionalities, (e.g. amino, hydroxyl, oximino, phenolic, silyl, carboxylic ester etc.) for loading of synthons, such as monomers, small molecules, oligomers and the like, suitable for carrying out a plurality of further reactions to synthesize the desired products. Each linker has a different functionality, one of them is chemically unstable under certain cleavage conditions (acid sensitive, base sensitive and the like) under which the functionality of the other linkers on the resin are inert. Accordingly, only the product at the unstable site is cleaved and individually separated from the reaction vessel while products at the stable site or sites remain attached to the support resin. The resin can be subsequently subjected to the further chemical manipulation for product synthesis or to subsequent cleavage steps under appropriate conditions so that a second product is cleaved and separated from the reaction vessel. Depending on the number of different linkers attached to the resin backbone, additional cleavage steps permit the sequential cleavage and separation of additional products. Therefore, products having different structures can be synthesized on a single solid support resin and can be released sequentially without cross contamination. The number of cleavage steps and cleavage conditions is dependent upon the number of different linker sites and the number of products to be released.

The invention further relates to a method for forming combinatorial libraries of compounds having different but related structures by solid phase methods. In accordance with the invention the method is carried out using a single multifunctionalized solid phase support resin and by sequentially separating and recovering the different products from the support resin.

ABBREVIATIONS

The following abbreviations are used herein and unless specifically indicated otherwise, designate the following groups or chemical compounds.

| | |
|---|---|
| Bn | Benzyl |
| Boc | tert-butoxycarbonyl |
| DEA | diethylamine |
| DCM | dichloromethane |
| DIC | diisopropylcarbodiimide |
| DMF | dimethylformamide |
| Fmoc | 9-fluorenylmethoxycarbonyl |
| HOBt | 1-hydroxybenzotriazole |
| HMBA | 4-hydroxymethylbenzoic acid |
| HMPA | 4-(hydroxymethyl)-phenoxyacetic acid |
| HMPB | 4-(4-hydroxymethyl-3-methoxyphenoxy)-butyric acid |
| HPLC | high-performance liquid chromatography |
| NMP | N-methylpyrrolidinone |
| PEG | poly(ethylene glycol) |
| PG | protecting group |
| TEA | triethylamine |
| TFA | trifluoroacetic acid |
| THF | tetrahydrofuran |

DESCRIPTION OF THE PREFERRED EMBODIMENTS

Figure 1:
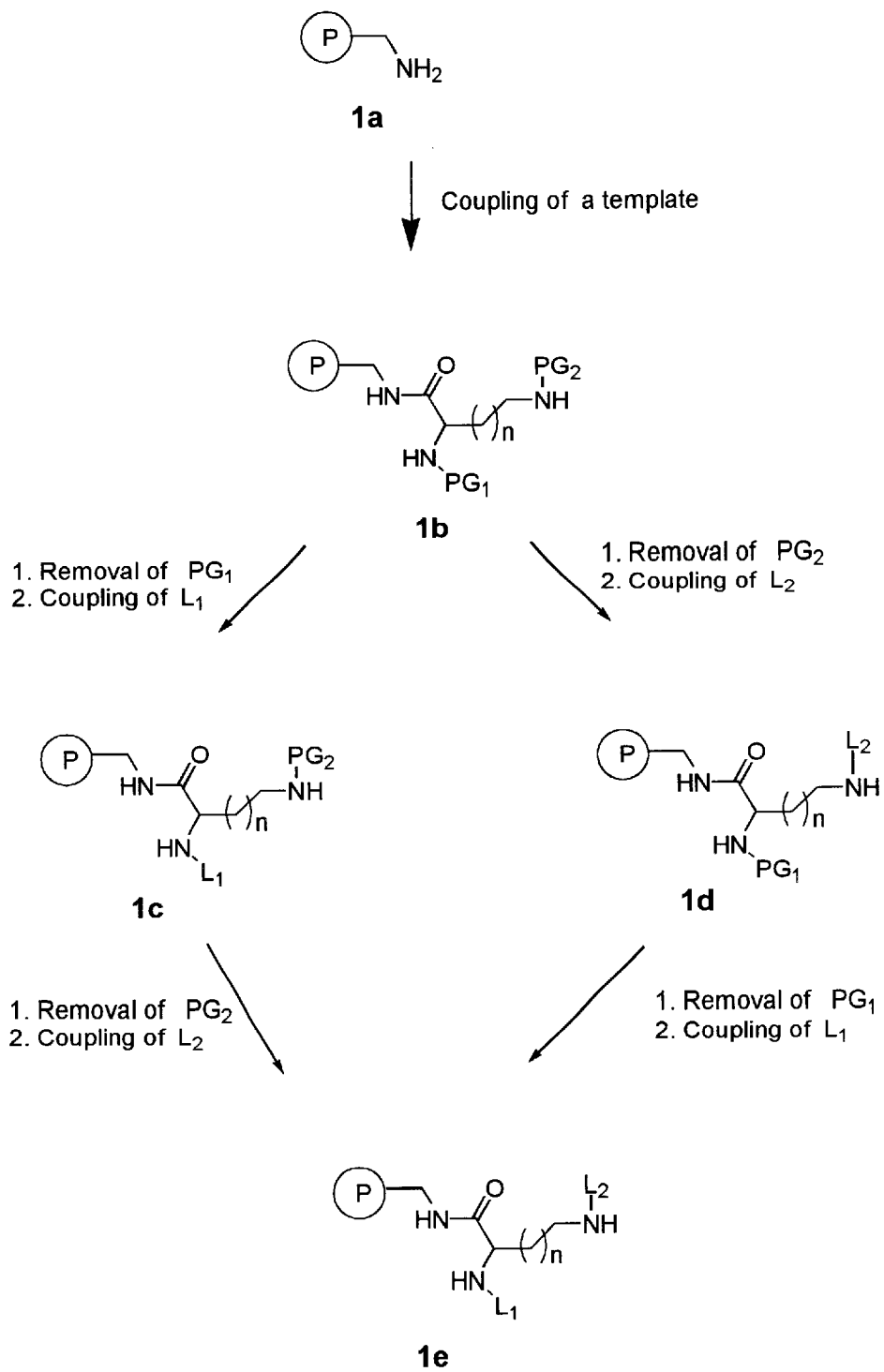
FIG. 1 is a schematic representation of the coupling of preferred linkers to a resin through a core template to form the multifunctionalized support resin in accordance with the invention.

In accordance with the invention the multifunctionalized resin is provided which is capable of supporting the simultaneous formation of two or more different small organic compounds in a single reaction vessel. The support resin can be represented by Formula 1:

Formula 1

Where P is any suitable resin backbone; X is selected from the group consisting of a covalent bond, C5–10 aryl, C5–10 heteroaryl, C1–5 alkyleneoxy, poly(C1–3 alkyleneoxy), C5–10 aryl C0–5alkoxy, C5–10 heteroaryl C0–5 alkyloxy, C5–10 aryl C0–5alkylamino, C5–10 heteroryl C0–5 alkylamino, the aryl and heteroaryl being optionally substituted with 1–3 groups of Rs;

T is a template possessing at least three attachment points that can be covalently bonded to X, $L_1$ and $L_2$, respectively, including but not limited to

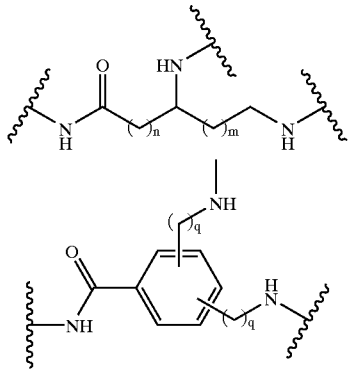

Wherein n and m are independently 0–3 and q is 0 or 1;

$L_1$ and $L_2$ are independently presented as Formula 2:

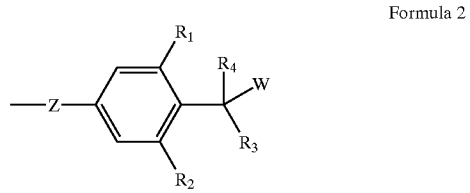

Formula 2

Where Z is selected from the group consisting of a covalent bond, O, S, NR, —C(O)—, —S(O)n—, C1–6 alkylene, C2–6 alkenylene, C4–6 cycloalkylene, C4–6 cycloalkenylene, C5–10 aryl C5–10 heteroaryl, carbonylC1–6alkylene, carbonylC1–6alkyleneoxy, carbonylC1–6alkylenethio, carbonylC2–6 alkenylene, carbonylC4–6 cycloalkylene, carbonylC4–6 cycloalkenylene, carbonylC5–10 aryl, or carbonylC5–10 heteroaryl, said aryl, heteroaryl, alkylene, alkenylene, cycloalkylene, and cycloalkenylene optionally substituted with 1–3 groups of Rs, wherein R represents hydrogen or C1–3 alkyl;

$R_1$ and $R_2$ are independently selected from the group consisting of H, C1–6alkyl, C1–6 alkyloxy, —SR, —S(O)R, —S(O)nR;

R3 and R4 are independently selected from the group consisting of H, C1–6 alkyl, C5–10 aryl, C5–10 heteroaryl, said aryl, heteroaryl, optionally substituted with 1–3 groups of Rs;

W is selected from the group consisting of OH, NHPG (PG represents a protecting group, including but not limited to Fmoc, Boc, Alloc, trfluoroacetyl).

The invention is further directed to a method for the production of combinatorial libraries using the multifunctionalized resin of the invention as the solid support resin. In accordance with the method of the present invention a substrate comprising a resin composition substituted with at least two or more linkers attached to a core template is placed in a single reaction vessel and is coupled by one or more synthons to produce structurally different small organic products. The products are selectively cleaved under conditions where only one site is unstable while all other sites are inert so that one product is cleaved and individually separated from the reaction vessel. The resin is subsequently subjected to a second cleaving step under conditions in which the next site is unstable so that a second product is cleaved and separated from the reaction vessel. The number of cleaving steps and conditions is dependent upon a number of linker sites and the number of products to be formed in the combinatorial library.

EXAMPLES OF THE MULTIFUNCTIONALIZED RESINS

Figure 2:
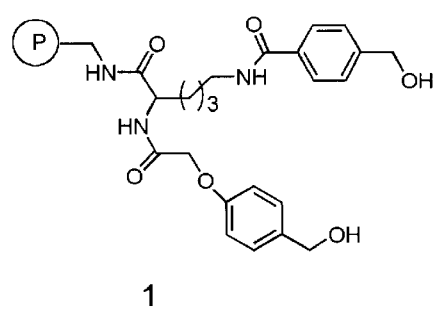
FIG. 2 is a schematic representation of multifunctionalized resins as set forth in examples 1–6.
Figure 2:
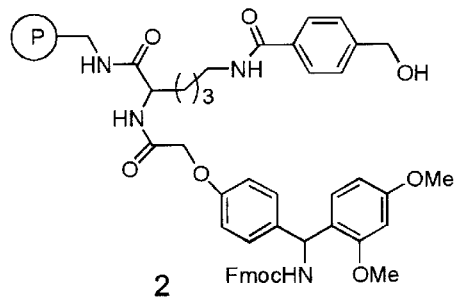
Figure 2:
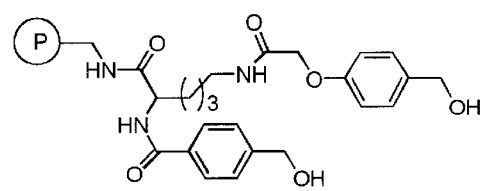
Figure 2:
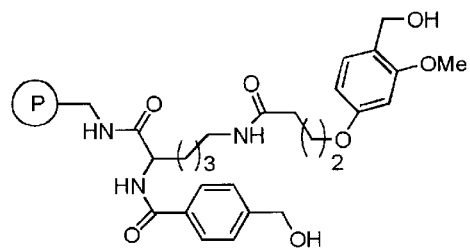
Figure 2:
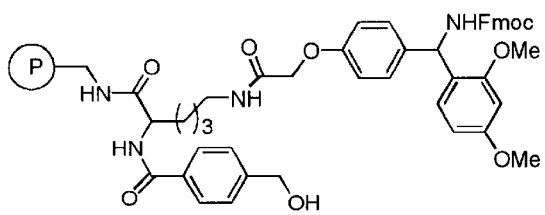
Figure 2:
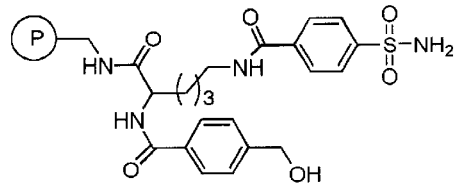
Figure 3:
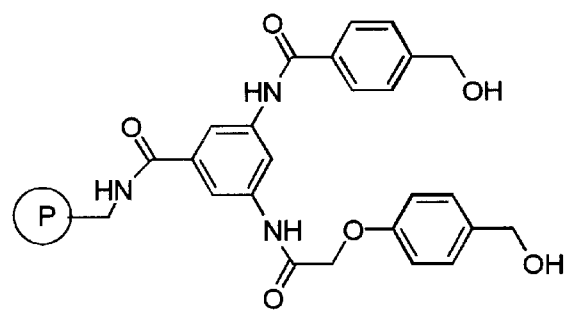
FIG. 3 is a schematic representation of the multifunctionalized resins as set forth in examples 7–8.
Figure 3:
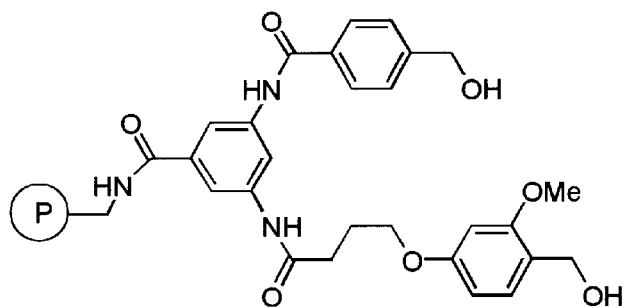

The following examples are by way of illustration of various aspects of the present invention and are not intended to be limiting thereof Design of the multifunctionalized resins is based on the differing stability of the linkers. The resin must possess a necessary template having multiple different attachment points, such as amino and carboxylic acid group, at which linkers can be introduced. Therefore, the multiple linkers can be coupled to this spacer that contains multiple attachment sites, such as lysine, diaminopropionic acid and diaminobenzoic acid moieties to give the multifunctionalized resins as shown in FIG. 2 and FIG. 3.

The resins obtained by this method keep optimal level of loading for each particular linkage unlike the method described by Bradley (M. Cardno and M. Bradley, Tetrahedron lett., 37, 135, 1996). For example, starting from the core resin, aminomethyl resin, the coupling of a template having at least three attachment points followed by coupling of HMPA and FMBA linkers gives the multifunctionalized resin without significantly losing the loading level for each hydroxy group. However, if the coupling of these two linkers are directly to the core resin, aminomethyl resin, the loading level is decreased at least in 50%. The detail protocols for their preparation are described in the following experimental part.

General Protocol-Reagent Systems and Test Methods

A general approach to the synthesis of these resins is illustrated in FIG. 1. As illustrated the support resin backbone is an aminomethyl resin and the template is a diamino acid. The protocol comprises the following steps:

Step 1 Coupling of the template with multiple protected attachment sites to resin backbone;

Step 2 Deprotect one of the attachment sites.

Step 3 Attach a first benzyl linker moiety to the template at the deprotected site.

Step 4 Deprotect the remaining attachment site.

Step 5 Attach a second benzyl linker moiety to the remaining deprotected attachment site.

Step 6 Repeat Steps 4 and 5 until all template attachment sites have a benzyl linker moiety attached.

Anhydrous solvents were purchased from Aldrich Chemical Company and used directly. Resins were purchased from Advanced ChemTech, Louisville, Ky., and used directly. The loading level ranged from 0.35 to 1.1 mmol/g. Unless otherwise noted, reagents were obtained from commercial suppliers and used without further purification. Preparative thin layer chromatography was preformed on silica gel pre-coated glass plates (Whatman PK5F, 150 Å, 1000 µm) and visualized with UV light, and/or ninhydrin, p-anisaldehyde, ammonium molybdate, or ferric chloride. NMR spectra were obtained on a Varian Mercury 300 MHz spectrometer. Chemical shifts are reported in ppm. Unless otherwise noted, spectra were obtained in $CDCl_3$ with residual $CHCl_3$ as an internal standard at 7.26 ppm. IR spectra were obtained on a Midac M1700 and absorbencies are listed in inverse centimeters. HPLC/MS analysis were performed on a Hewlett Packard 1100 with a photodiode array detector coupled to a Micros Platform II electrospray mass spectrometer. An evaporative light scattering detector (Sedex 55) was also incorporated for more accurate evaluation of sample purity. Reverse phase columns were purchased from YMC, Inc. (ODS-A, 3 µm, 120 Å, 4.0×50 mm).

Solvent system A consisted of 97.5% MeOH, 2.5% $H_2O$, and 0.05% TFA. Solvent system B consisted of 97.5% $H_2O$, 2.5% MeOH, and 0.05% TFA. Samples were typically acquired at a mobile phase flow rate of 2 mL/min involving a 2 minute gradient from solvent B to solvent A with 5 minute run times. Resins were washed with appropriate solvents (100 mg of resin/1 mL of solvent). Technical grade solvents were used for resin washing.

FIG. 2 and FIG. 3 illustrate the multifunctionalized support resins prepared in accordance with the protocols set out in the following examples.

Example 1

Preparation of Compound 1 in FIG. 2:

Aminomethyl polystyrene (10 g, 8 mmol) was placed in a 250 mL reaction vessel, then a 0.5 M solution of Boc-Lys (Fmoc)-OH in DMF (64 mL, 32 mmol) and a 2 M solution of HOBt in DMF (16 mL, 32 mmol) were added followed by addition of a 2.0 M solution of DIC (16 mL, 32 mmol) in DCM. The reaction mixture was mixed on a shaker station for 3 h, then filtered and washed with DMF (3×), DCM/MeOH (3×), and dried in vacuo. The above obtained resin was then treated with 25% piperidine in DMF for 30 min, filtered and washed with DMF (2×), MeOH/DCM (3×) and DCM (2×).

The Boc-Lys-aminomethyl resin was then added to a mixture of 60 mL of a 0.5 M solution of 4-hydroxymethylbenzoic acid in DMF and 15 mL of a 2 M solution of HOBt in DMF. A 0.5 M solution of DIC in DCM (15 mL) was added. The reaction mixture was stirred for 3 h at room temperature. Filtration followed by washing with DMF (3×), MeOH/DCM (3×), DCM (3×), to give the resin which was dried in vacuo. It showed negative in the Kaiser test.

The resin obtained above was treated with 100 mL of 25% TFA/DCM for 30 min, filtered and washed and neutralized under standard conditions. The deprotected resin was then mixed with 60.0 mL of a 0.5 M solution of hydroxymethylphenoxy acetic acid in DMF containing an equimolar amount of HOBt, and 60 mL of a 0.5 M solution of DIC in DCM. After 3 h, the suspension was filtered, washed as described above and dried to give the desired HMBA/HMPA/Lysine resin with approximately 0.6 mmol/g loading for HMPA and HMBA, respectively.

Example 2

Preparation of Compound 2 in FIG. 2:

The same procedure was followed as described in the Example 1 except the HMPA linker was replaced by Knorr linker.

Example 3

Preparation of Compound 3 in FIG. 2:

The same procedure was followed as described in the Example 1 except Boc-Lys(Fmoc)-OH was replaced by Fmoc-Lys(Boc)-OH.

Example 4–6

Preparation of Compounds 4, 5 and 6 in FIG. 2:

The same procedure was followed as the preparation of the Example 3 except HMPA linker was replaced by the various corresponding linkers, HMPB linker (Compound 4), Knorr linker (Compound 5) and aminosulfonyl benzoic acid linker (Compound 6).

Example 7 and 8

Preparation of Compound 7 & 8 in FIG. 3:

Aminomethyl polystyrene (0.8 mmol/g) was treated with 3-amino-5-nitrobenzoic acid (3 equiv.), 0.5 M HBTU/HOBt in DMF (3 equiv.) and DIEA (12 equiv.) for 2 h. The resin was filtered and washed with DMF (3x), DCM/MeOH (3x), and dried in vacuo. The above obtained resin was then treated with 4-acetoxymethylbenzoyl chloride (10 equiv.) freshly prepared from the corresponding acid and DIEA (20 equiv.) in DCM for 4–5 h, followed by DMF and DCM washes. The resin was then treated with 2M $SnCl_2$ in DMF overnight. The mixture was filtered and washed with DMF (3x), DCM/MeOH (3x), and dried in vacuo. The second linker, Ac-FMPA or Ac-HMPB was introduced under the same condition as the first. The acetyl group was removed by the treatment of the resin with 0.5 M LiOH in 1:1 THF/$H_2O$ overnight.

APPLICATIONS OF THE MULTIFUNCTIONALIZED RESINS TO SOLID PHASE SYNTHESIS OF ORGANIC COMPOUNDS

The following examples illustrate the use of multifunctionalized supports designed in accordance with present invention in the solid support synthesis of organic compounds. The compounds synthesized in the examples and the particular multifunctionalized support resins utilized therein are for purposes of illustration and the examples should not be construed as limiting the invention. The reaction sequences of the following examples are illustrated in FIGS. 4–11.

Figure 4:
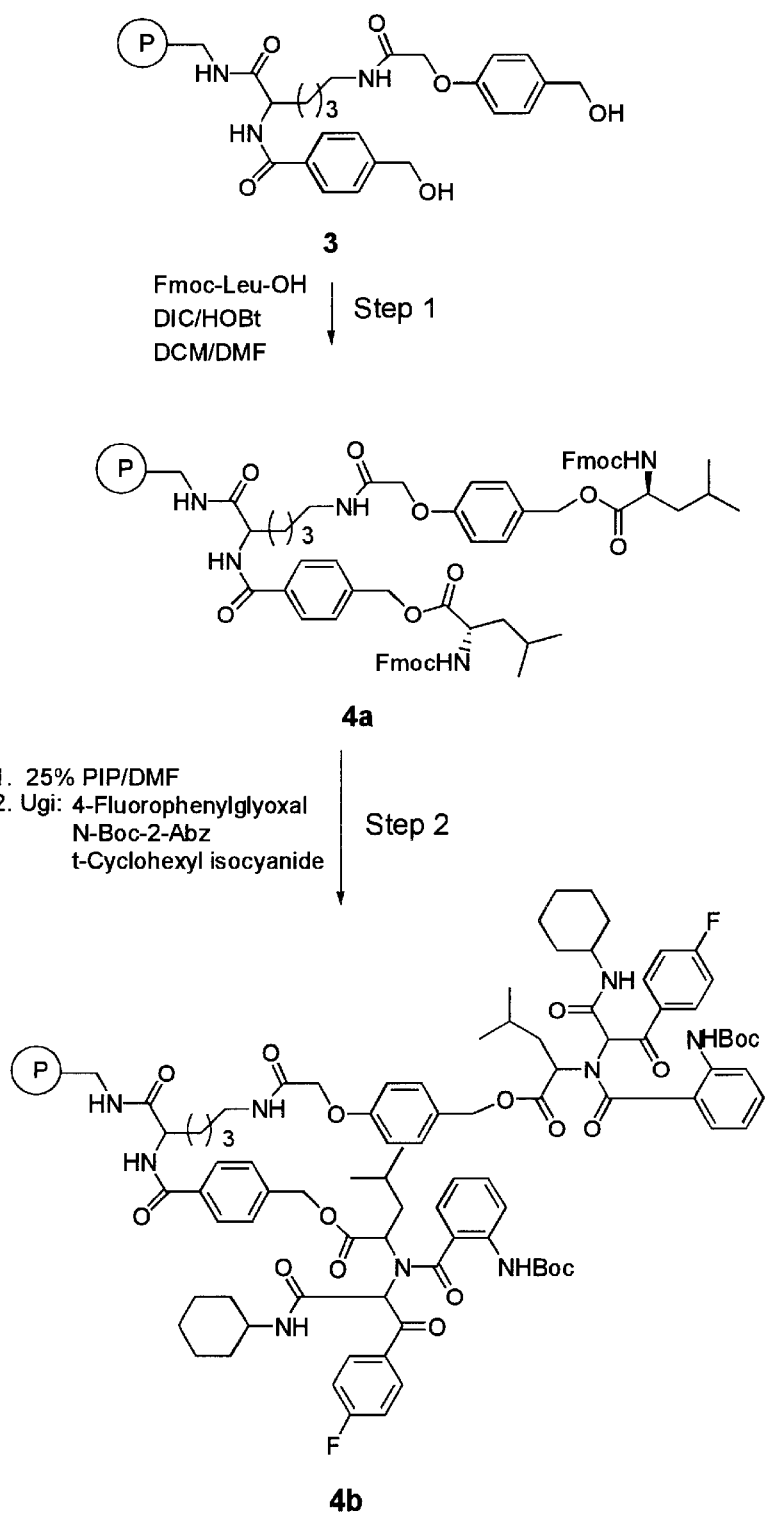
FIG. 4 and FIG. 5 are schematic representations of the solid phase synthesis of the products as set forth in example 9.
Figure 5:
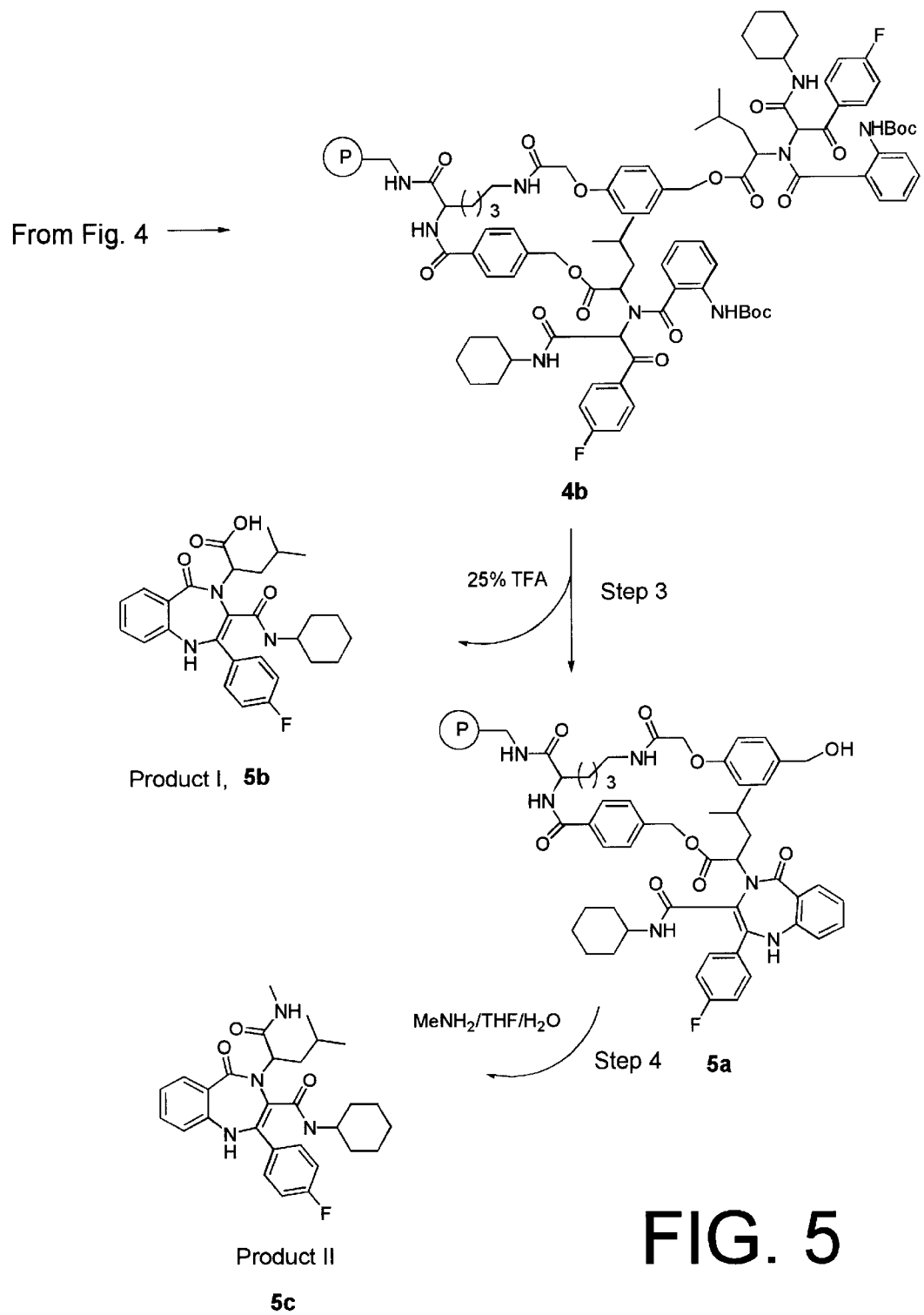
Figure 6:
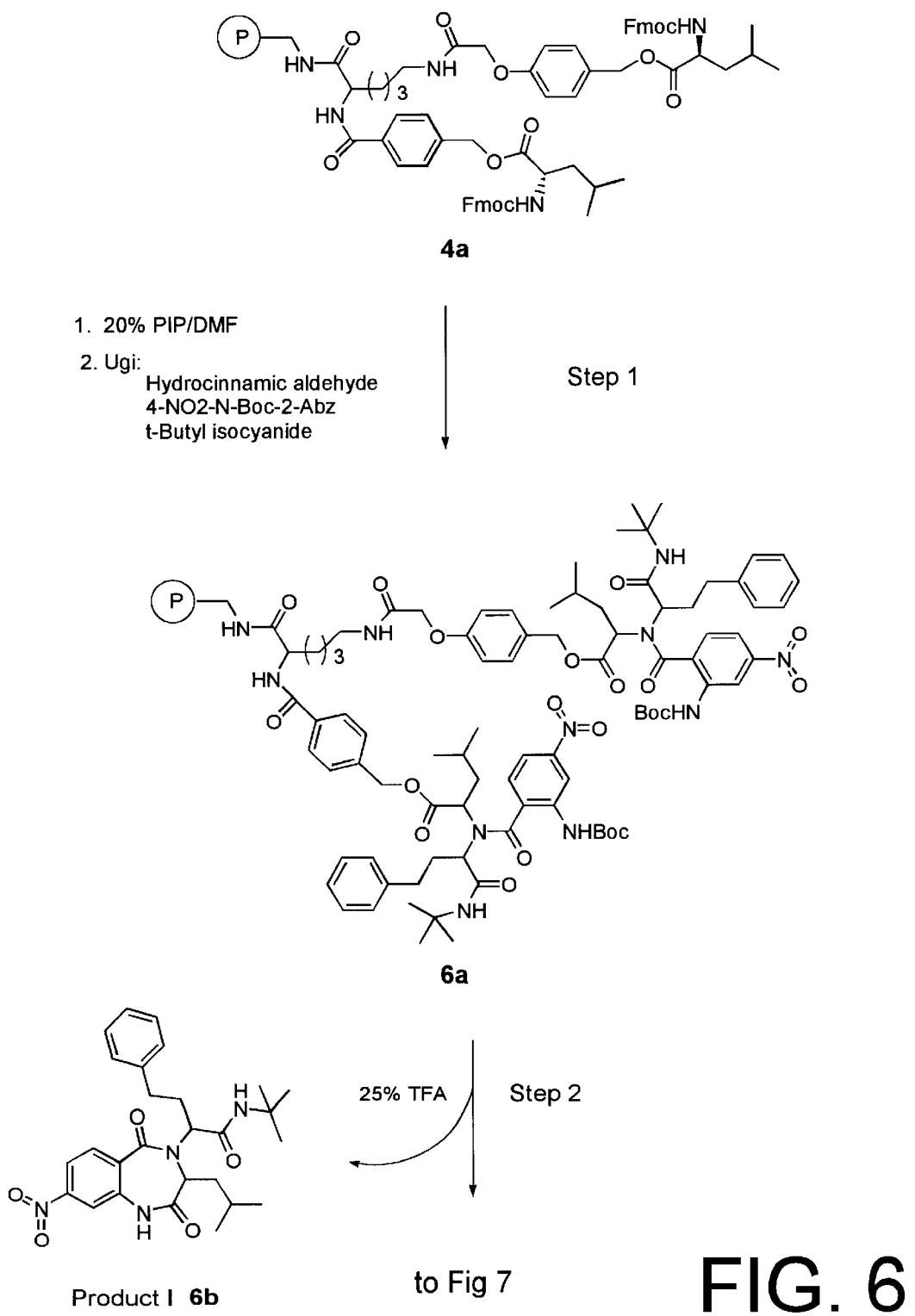
FIG. 6 and FIG. 7 are schematic representations of the solid phase synthesis of products as set forth in example 10.
Figure 7:
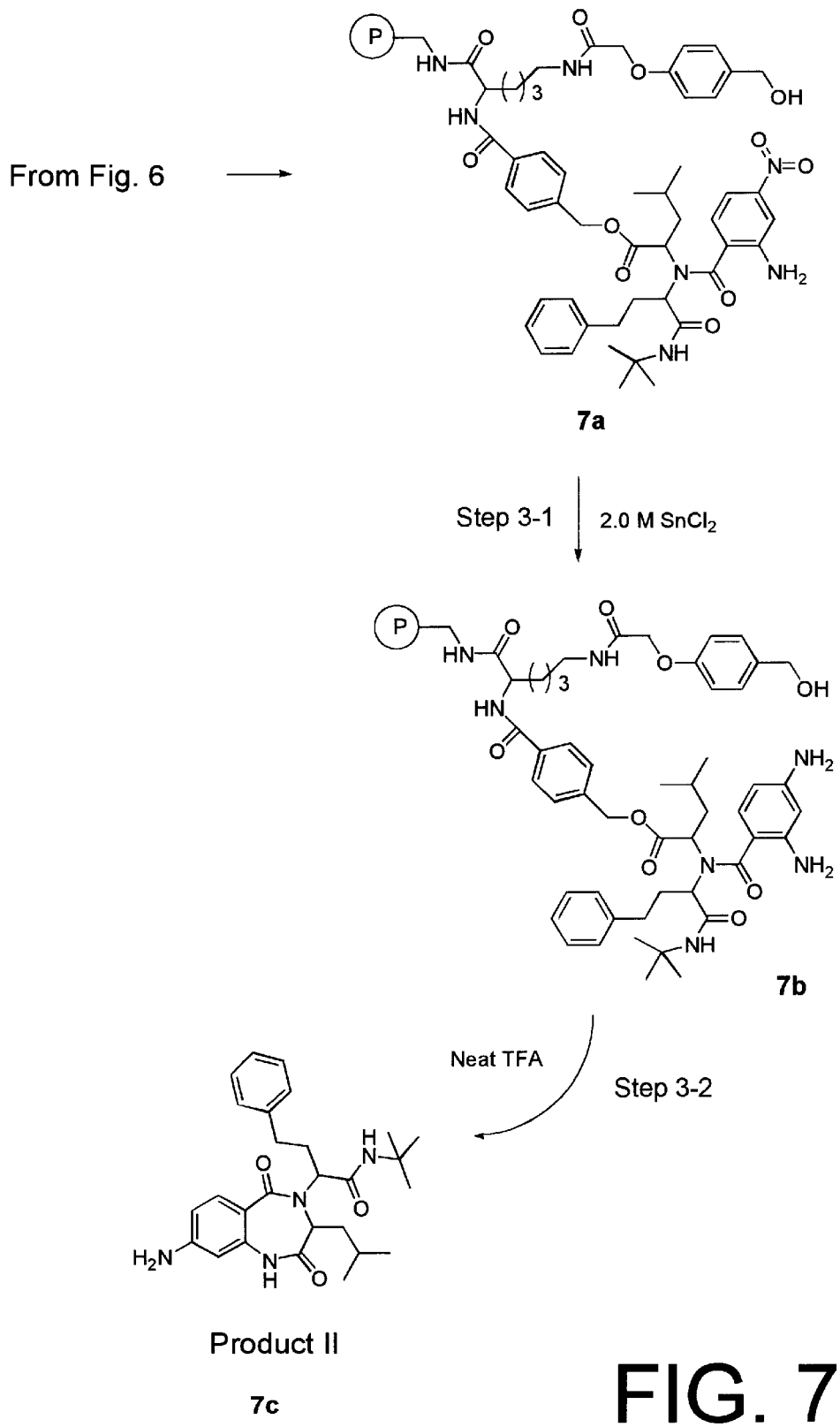

Example 9 (FIGS. 4–5)

Step 1. Coupling of an Fmoc Amino Acid to the Resin:

A multifunctionalized resin (2 g, compound 3 in FIG. 2) was placed in a 25 mL reaction vessel. To it was added 4.8 mL of a 0.5 M solution of Fmoc-Leu-OH in 2:1 DCM/DMF containing an equimolar amount of HOBt. A 0.02 M solution of DMAP in DCM (4 mL) and DIC (375 μL) were added. After the reaction mixture was shaken for 3 h, the resin was filtered, washed as usual and dried in vacuo.

Step 2. Ugi Reaction:

The above amino acid coupled resin (1 g) was introduced into a 50 mL reaction vessel. The Fmoc protecting group was removed by the treatment with 10 mL of 20% piperidine in DMF for 20 min at room temperature. The resin was then filtered and washed with DMF (2x) and DCM/MeOH (3x), and dried in vacuo.

To the resin was then added a 1.0 M solution of 4-fluorophenyglyoxal in THF (8.0 mL), a 1.0 M solution of 2-N-Boc-aminobenzoic acid in 1:1 THF/MeOH (8.0 mL), a 1.0 M solution of $ZnCl_2$ in diethylether (4 mL) and a 1.0 M solution of cyclohexyl isocyanide in MeOH (8 mL). The suspension was shaken at room temperature for 2 days. The resin was filtered and washed with DMF (3x), DCM/MeOH (3x).

Step 3. Selective Cleavage of the First Reaction Product From the HMPA Linker:

The Boc protecting group of the Ugi products on the resin was removed by treatment with 25% TFA in DCM with simultaneous cyclization to form the first benzodiazepine. The cleavage solution was filtered and the resin was rinsed with 5 mL of 5% TFA solution in DCM. Concentration of the combined filtrates provided the unpurified product (>80% purity by LC-MS), which was then purified by silica gel chromatography and fully analyzed. $^1$HNMR ($CDCl_3$+$CD_3OD$): δ 10.2 (br, 1H), 7.82 (t, 1H), 7.56 (dd, 1H), 7.46 ((t, 1H), 7.42 (dd, 1H), 7.29 (m, 1H), 7.18 (m, 1H), 6,97–6.71 (m, 6H), 6.64 (m, 1H), 5.46 (br, 1H), 5.0 (br, 1H), 3.72 (m, 1H), 3.37 (m, 1H), 3.11 (m, 1H), 2.75 (m, 1H), 1.59 (m, 2H), 1.43 (m, 2H), 1.1–0.9 (m, 6H).

Step 4. Cleavage of the Second Reaction Product From the HMBA Linker:

The resin was washed with DCM (3x), then neutralized with 1.0 M DIEA/DCE and washed again with MeOH/DCM (3x). The second product was cleaved as an N-methyl amide by the treatment with a 1:1 mixture of 48% aqueous solution of methylamine and THF at room temperature overnight. Filtration followed by concentration gave the crude product which was purified by the flash chromatography. $^1$HNMR ($CDCl_3$+$CD_3OD$): δ 7.92 (t, 1H), 7.62 (dd, 2H), 7.25 (m, 4H), 7.10 (m, 1H), 6.98 (m, 1H), 6.87 (m, 3H), 5.90 (s, 1H), 5.51 (t, 1H), 5.28 (dd, 1H), 5.20 (s, 1H), 4.25 (dd, 1H), 3,47 (dd, 1H), 3.30 (dd, 1H), 3.11 (m, 1H), 2.69 (d, 3H), 2.22 (m, 2H), 1.46 (m, 3H), 1.04 (m, 2H), 0.88 (m, 2H).

Example 10 (FIGS. 6 & 7):

Step 1: Ugi Reaction:

The Fmoc-Leu coupled support resin 4a prepared in the Example 9 (800 mg) was de-protected with 25% piperidine in DMF under the standard conditions. The resin was then mixed with 8 mL of a 1.0 M solution of 4-Nitro-N-Boc-2-aminobenzoic acid in THF, 3.3 mL of a 2.0 M solution of hydrocinnamaldehyde in methanol and 3.3 mL of a 2.0 M solution of t-butyl isocyanide in MeOH. The mixture was stirred for 2 days at room temperature. The resin was filtered, washed with DMF (3x), DMC/MeOH (3x), and Step 2. Deprotection and Cleavage of the First Product:

The above resin was treated with 25% TFA in DCM for 30 min. The cleavage solution was filtered and the resin was rinsed with 5% TFA solution in DCM. The combined filtrates were concentrated to give the first benzodiazepine-dione in >90% purity. It was purified by silica gel chromatography. $^1$HNMR ($CDCl_3$+$CD_3OD$): δ 9.86 (br s, 1H), 8,26 (d, 1H, J=8.7 Hz) 8.05 (dd, 1H, J=8.7, 2.1 Hz), 7.94 (d, 1H, J=2.1 Hz), 7.29 (td, 1H), 7.22–7.07 (m, 4H), 6.25 (s, 1H), 5.08 (dd, 1H, J=7.8, 7.20 Hz), 4.,70 (dd, 1H, J=10.8, 3.9 Hz), 2.76 (m, 1H), 2.54 (m, 2H), 2.29 (m, 1H), 2.11 (m, 1H), 1.90 (m, 1H), 1.57 (m, 1H), 1.35 (s, 9H), 0.94 (d, 3H, J=6.3 Hz), 0.77 (d, 3H, J=6.3 Hz).

Step 3. Reduction of the Nitro Group and Cleavage of the Second Product:

The remaining resin was washed with DCM (3×) and neutralized with 1 M DIEA in DCE, further washed with DCM/MeOH (3×) and dried in vacuo. It was then treated with 9.0 mL of a 2.0 M $SnCl_2$ solution in NMP at room temperature for 18–20 h. The resin was filtered and washed with NMP (2×), 1:1 MeOH/$H_2O$ (2×), then MeOH/DCM (3×). The resin was then treated with 8.0 mL of neat TFA overnight. The cleavage solution was filtered and washed with 20% TFA in DCM (2×). The combined filtrates were concentrated to provide the unpurified product in >90% purity. The pure product was obtained by flash chromatography on silica gel. $^1$HNMR ($CDCl_3$+$CD_3OD$): δ 9.38 (brs, 1H), 784 (d, 1H, J=8.7 Hz), 7.26–7.06 (m, 5H), 6,60 (s, 1H), 6.49 (dd, 1H, J=8.7, 2.4Hz), 6.30 (d, 1H), J=2.40), 5.05 (dd, 1H, J=8.4, 6.9 Hz), 4.43 (dd, 1H, J=11.1, 4.5 Hz), 3.08 (m, 1H), 2.49 (m, 2H), 2.20 (m, 1H), 2.08 (m, 1H), 1.61 (m, 1H), 1,54 (m, 1H), 1.32 (s, 9H), 0.89 (d, 3H, J=6.4 Hz), 0.75 (d, 3H, J=6.4 Hz).

Figure 8:
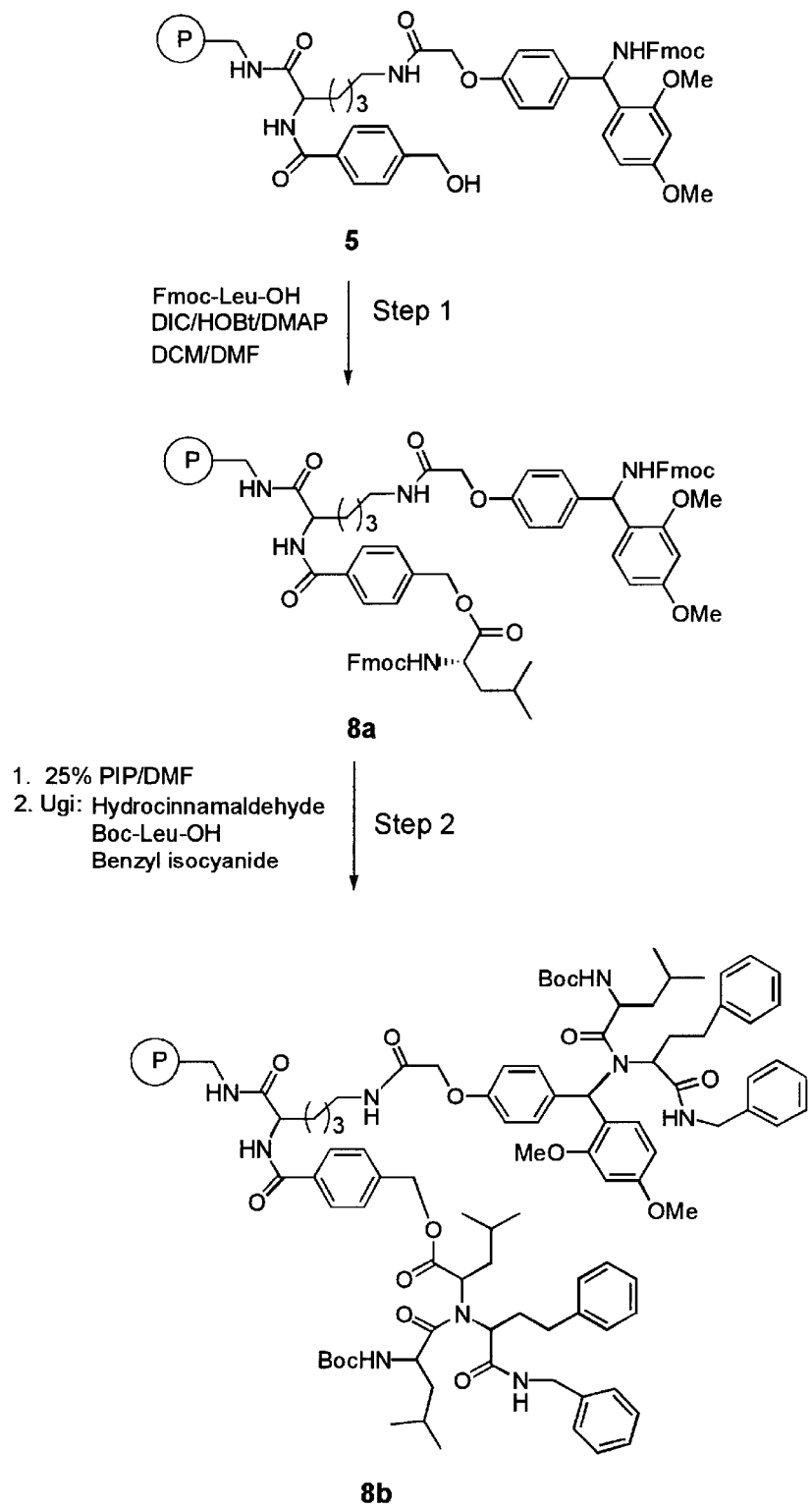
FIG. 8 and FIG. 9 are schematic representations of the solid phase synthesis of products as set forth in example 11.
Figure 9:
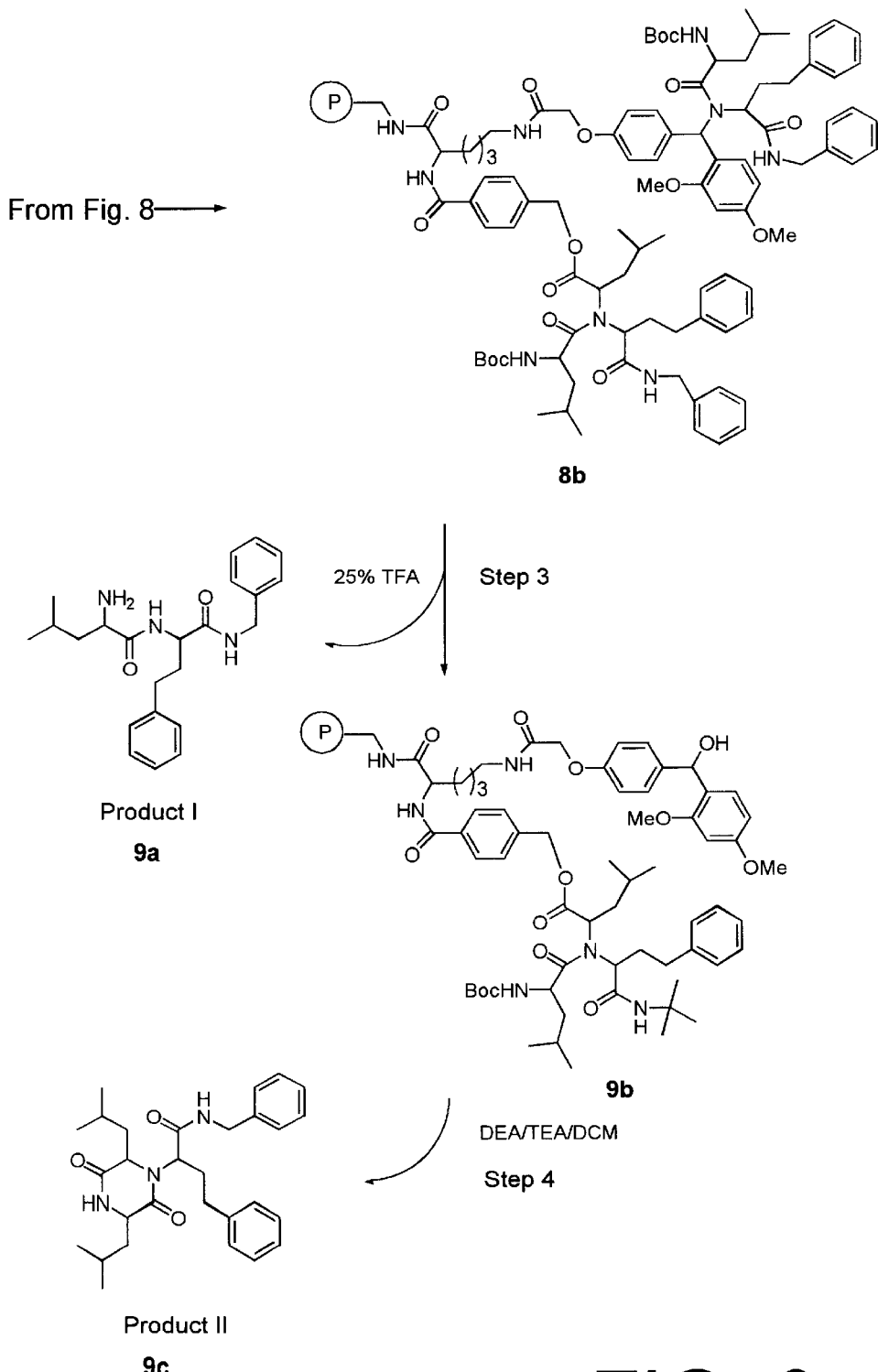

Example 11 (FIGS. 8–9)

Step 1. Coupling of an Amino Acid to the Resin:

A multifunctionalized resin 5 (1 g) was placed in a 25 mL reaction vessel. A 0.5 M solution of Fmoc-Leu-OH in 2:1 DCM/DMF (8.0 mL) containing an equimolar amount of HOBt was added followed by addition of 4.0 mL of 0.02 M solution of DMAP in DCM and 375 μL of DIC. After mixing for 3 h at room temperature, the resin was filtered and washed and dried in vacuo.

Step 2. Deprotection and Ugi Reaction:

The resin (1 g) was treated with 20% piperidine in DMF for 30 min. Filtration followed by washing with DMF (2×) and DCM/MeOH (3×) gave the de-Fmoc resin which was then mixed with 8.0 mL of 1.0 M solution of hydrocinnamaldehyde in THF, 8.0 mL of 1.0 M solution of Boc-Leu-OH in 1:1 THF/MeOH, and 8.0 mL of 1.0 M solution of t-butyl isocyanide in MeOH. The slurry was stirred at room temperature for 2 days. The usual work up of the reaction mixture was applied.

Step 3. Cleavage of the First Product:

The Boc protecting group of both Ugi products on the resin was removed by the treatment with 25% TFA in DCM with simultaneous cleavage of the first product. The resin was rinsed with 5% TFA in DCM. The filtrates were combined and concentrated to give the crude product in >90% purity (confirmed by LC-MS) which was purified by silica gel chromatography. $^1$HNMR ($CDCl_3$): δ 7.95 (d, 1H, NH), 7.0–7.3 (m, 10H, aromatic-H), 6.97 (m, 1H, NH), 4.3–4.4 (m, 3H, $CH_2$, CH), 3.5 (m, 1H, CH), 3.0 (brs, 2H, $NH_2$), 2.6 (t, 2H, $CH_2$), 2.1 (m, 1H, CH), 2.0 (m, 1H, CH), 1.6 (m, 2H, $CH_2$), 1.4 (m, 1H, CH), 0.8 (m, 6H, 2 $CH_3$).

Step 4. Cleavage of the Second Product:

The resin was washed with DCM, MeOH and then neutralized with 1.0 M DEA in DCE. The resin was further washed with MeOH and DCM (3×), then treated with 10 mL of a mixture of 1:1:1 DEA/TEA/DCM for 6 h. The cleavage solution was filtered and concentrated to provide the crude product in >90% purity, which was purified by silica gel chromatography. $^1$HNMR ($CDCl_3$): d 7.7 (t, 1H, NH), 7.0–7.2 (m, 10H, aromatic-H), 6.4 (d, 1H, NH), 4.4–4.5 (dd, 2H, $CH_2Ph$), 3.7–3.8 (m, 2H), 2.4–2.5 (m, 3H, $CH_2$, CH), 2.3 (m, 1H, CH), 1.3–1.4 (m, 8H, 3$CH_2$, 2CH), 0.7–0.8 (m, 12H, 4$CH_3$).

Figure 10:
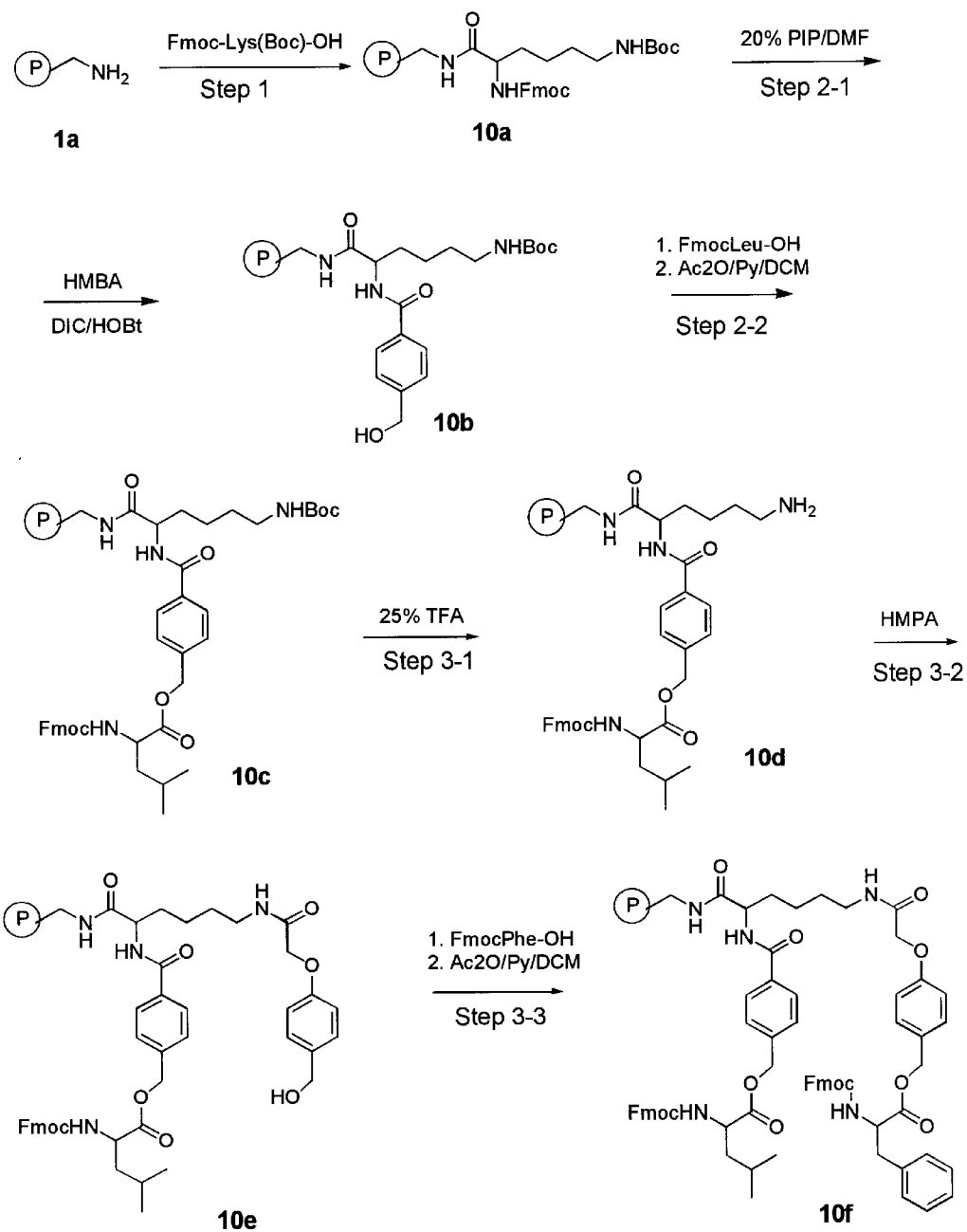
FIG. 10 and FIG. 11 are schematic representations of the solid phase synthesis of products as set forth in example 12.
Figure 11:
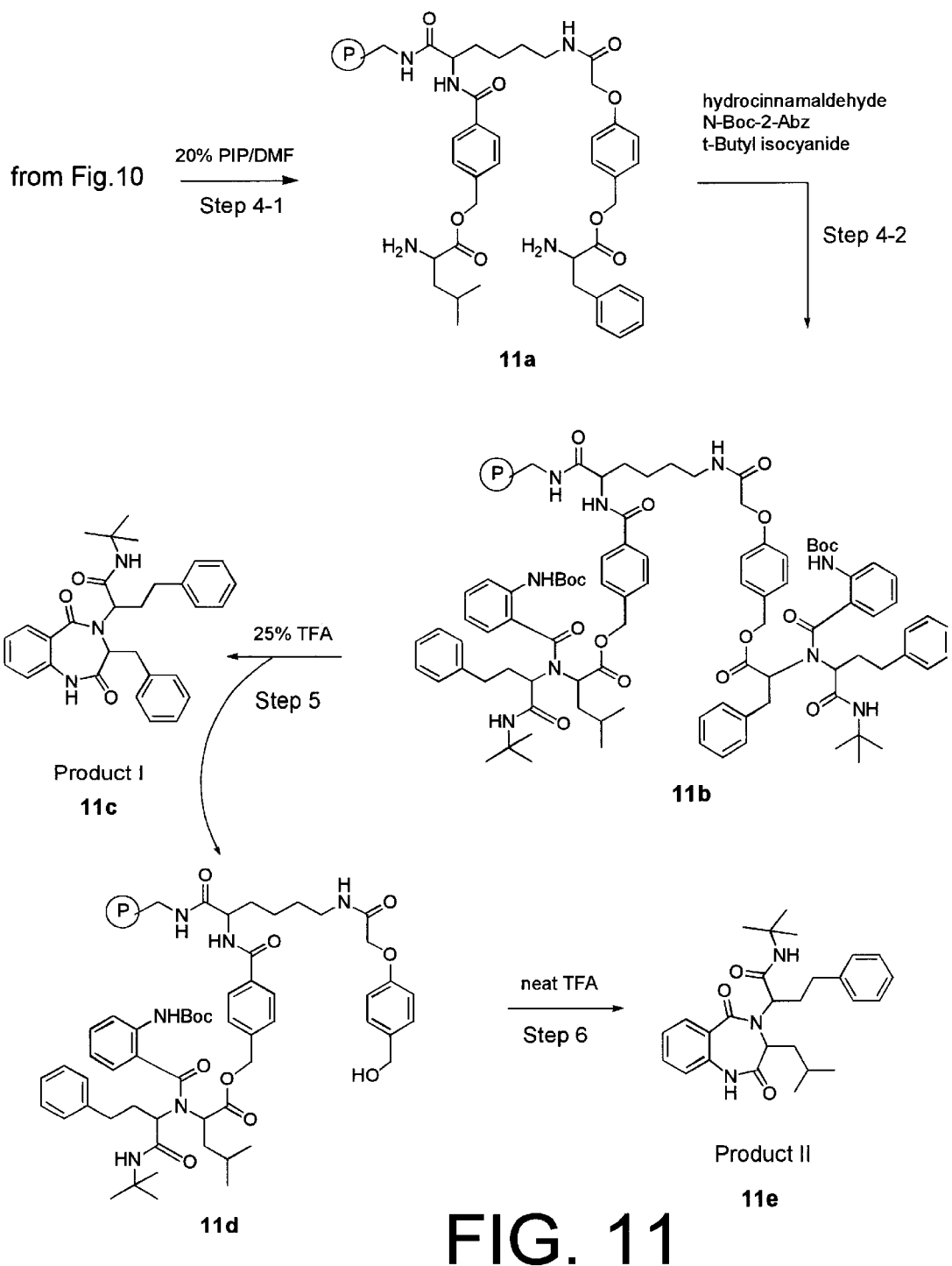

Example 12 (FIGS. 10–11)

Step 1. Coupling of Boc-Lys(Fmoc)-OH to Aminomethyl Resin:

Aminomethyl polystyrene (5 g, 4 mmol) was placed in a 100 mL reaction vessel, then a 0.5 M solution of Fmoc-Lys (Boc)-OH in DMF (100 mL) containing an equimolar amount of HOBt was added followed by 16 mL of a 2.0 M solution of DIC in DCM. The reaction mixture was mixed on a shaker station for 3 h, then filtered and washed with DMF (3×), DCM/MeOH (3×), and dried in vacuo.

Step 2. Attachment of the HMBA Linker and the Coupling of the First Amino Acid:

Fmoc-Lys(Boc)-amino methyl resin (2.5 g) was treated with 25% piperidine in DMF for 30 min, filtered and washed with DMF (2×), MeOH/DCM (3×) and DCM (2×).

The deprotected Lys(Boc)-aminomethyl resin was then treated with 15.0 mL of a 0.5 M solution of 4-hydroxymethylbenzoic acid in DMF containing equimolar amount of HOBt. A 0.5 M solution of DIC solution in DCM (15 mL) was added. The reaction mixture was stirred for 3 h at room temperature. Filtration followed by washing with DMF (3×), MeOH/DCM (3×), DCM (3×), to give the resin which was dried in vacuo. It showed negative in the Kaiser test.

To the resin prepared above were added a 0.5 M solution of Fmoc-Leu-OH in 2:1 DCM/DMF (12 mL, 6 mmol) and a 0.8 M solution of DIC in DCM (7.5 mL) containing 26 mg DMAP. The suspension was mixed for 3 h at room temperature. Filtration followed by washing gave the resin which was dried in vacuo. The resin was capped by the treatment with 30 mL of a 2.0 M acetic anhydride solution in DCM containing pyridine (60 mmol) and DMAP (40 mg, 0.2 equiv.). The slurry was stirred for 2 h at room temperature. The resin was filtered, washed and dried.

Step 3. Attachment of the HMPA Linker and Coupling of the Second Amino Acid:

The resin obtained above (2.5 g) was treated with 25 mL of 25% TFA/DCM for 30 min, filtered and washed under standard conditions. The deprotected resin was then mixed with 15.0 mL of a 0.5 M solution of hydroxymethylphenoxy acetic acid in DMF containing an equimolar amount of HOBt, and 15.0 mL of a 0.5 M solution of DIC in DCM. After 3 h, the resin was filtered, washed as described above and dried. The resin was acylated with Fmoc-Phe-OH under the same conditions as the coupling of the first amino acid. After the acylation, the resin was capped by the treatment with acetic anhydride as described above.

Step 4. Ugi Reaction:

The Fmoc protecting group was removed under standard conditions. The resin (625 mg) was then treated with a 1.0 M solution of N-Boc-2-aminobenzoicacid in THF (10 mL, 10 mmol), hydrocinnamic aldehyde (1.32 mL, 10 mmol) and a 1.0 M solution of t-butyl isocyanide (10 mL, 10 mmol). The slurry was stirred for 2 days, filtered and washed as usual.

Step 5. Cleavage of the First Product:

The resin was mixed with 6.5 mL of 25% TFA in DCM for 30 min. The cleavage solution was then filtered and the resin was rinsed with 5% TFA in DCM. The combined filtrates were concentrated to provide the unpurified product in more than 85% purity confirmed by LC-MS, which was purified by the flash chromatography on silica gel. $^1$HNMR ($CDCl_3$): δ 9.2 (s, 1H), 8.01 (dd, 2H, 8.1, 1.8 Hz), 7.35–7.10 (m, 6H), 6.97 (dd, 2h), 6.81 (dd, 1H), 5.77 (s, 1H), 5.12 (dd, 1H, J=8.1, 5.7), 4,57 (t, 1H), 2.75 (dd, 2H), 2.63 (m, 1H), 5,12 (dd, 1H, J=8.1, 5.7), 4.57 (t,1H), 2.75 (dd, 2H), 2.63 (m, 1H), 2.48 (ddd, 1H), 2.19 (m, 2H), 1.24 (s, 9H).

Step 6. Cleavage of the Second Product:

The remaining resin was washed with DCM (3×), 1M DIEA in DCM (1×), DCM/MeOH (3×) and DEM (3×). The resin was then treated with 6.5 mL of neat TFA at room temperature overnight. The second benzodiazepine was cleaved, and the cleavage solution was filtered and concentrated to give the unpurified product which was purified by flash chromatography on silica gel.

$^1$H NMR (CDCl$_3$+CD$_3$OD): δ 7.87 (dd, 2H, J=8.1, 1.5), 7.42 (dt, 2H, J=8.1, 1.5), 7.22–7.01 (m, 3H), 6.93 (m, 2H), 4.99 (dd, 1H, J=7.8, 6.9 Hz), 4.46 (dd, 1H, J=11.1, 4.8 Hz), 2.65 (m, 1H), 2.47 (m, 2H) 2.13 (ddd, 1H), 2.01 (ddd, 1H), 1.38 (m, 2H), 1.24 (s, 9H), 1.05 (m, 1H), 0.79 (d, 3H, J=6.3 Hz), 0.62(d, 3H, J=6.3 Hz).

As mentioned above, the support resin carrying the template and the benzyl linker moieties in accordance with the invention may also have directly attached one or more additional linkers. These include but are not limited to linkers that are acid labile, base labile, nucleophillic labile, electrophillic labile, photo labile, oxidation labile or reduction labile. Such linkers can be directly attached to remaining sites on the resin backbone through standard chemical coupling reaction techniques. The functionality and resultant chemical stability of any such additional linkers must not be the same as the chemical stability of the benzyl linker moieties described above so that synthesized products can be sequentially removed from the support resin. It will be understood that a large number of strategies are available for attachment of various linkers in addition to the multifunctionalized benzyl linkers discussed above. It will be understood that the selection of linkers for direct attachment to the resin is dependent upon, among other factors, the number and type of products being synthesized.

As will be understood by those skilled in the art, various arrangements which lie within the spirit and scope of the invention other than those described in detail in the specification will occur to those persons skilled in the art. It is therefor to be understood that the invention is to be limited only by the claims appended hereto.

Having described the invention, we claim:

1. A multifunctionalized solid support for the solid support synthesis of at least two different compounds, said solid support having the structure:

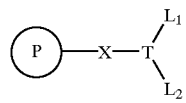

wherein P is a resin backbone, T is a diamino acid moiety template having at least three attachment points, X is a covalent bonding entity for attachment of T to P and L$_1$ and L$_2$ are independently different benzyl linker moieties having the formula:

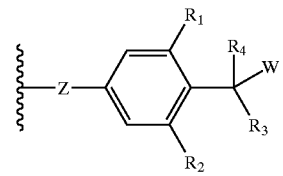

wherein Z is selected from the group consisting of a covalent bond, O, —C(O)—, C1–6 alkylene, C5–10 aryl, carbonylC1–6alkylene, carbonylC1–6alkyleneoxy, carbonyl C5–10 aryl and carbonyl C5–10 heteroaryl, said alkylene, aryl and heteroaryl groups being substituted with H or C1–3 alkyl;

R$_1$ and R$_2$ are independently selected from the group consisting of H, nitro, halo and C1–6alkoxy;

R$_3$ and R$_4$ are independently selected from the group consisting of H, C1–6 alkyl, C5–10 aryl and C5–10 heteroaryl, said alkyl, aryl and heteroaryl groups being substituted with H, C1–3 alkyl or C1–3 alkoxy; and W is selected from the group consisting of OH, NH$_2$ and NHpg where pg is a protecting group.

2. The multifunctionalized solid support of claim 1 wherein said benzyl linker moieties have different fuctionalities and are selectively cleavable.

3. The multifunctionalized solid support resin of claim 1 wherein said benzyl linker moieties independently comprise 4-(hydroxymethyl)-phenoxyacetic acid (HMPA) and 4-hydroxymethylbenzoic acid (HMBA).

4. The multifunctionalized solid support resin of claim 3 having the structure:

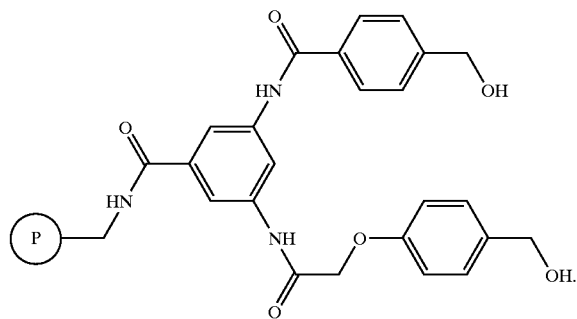

5. The multifunctionalized solid support resin of claim 1 wherein T is lysine and said benzyl linker moieties independently comprise 4-hydroxymethylbenzoic acid (HMBA) and 4-(hydroxymethyl)-phenoxyacetic acid (HMPA).

6. The multifimctionalized solid support resin of claim 5 having the structure:

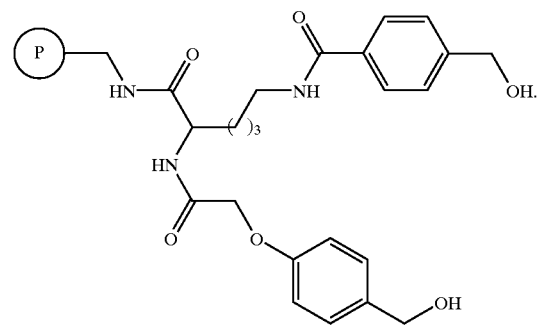

7. The multifunctionalized solid support resin of claim 1 wherein T is lysine and said benzyl linker moieties independently comprise 4-hydroxymethylbenzoic acid (HMBA) Knorr linker.

8. The multi-functionalized solid support resin of claim 7 having the structure:

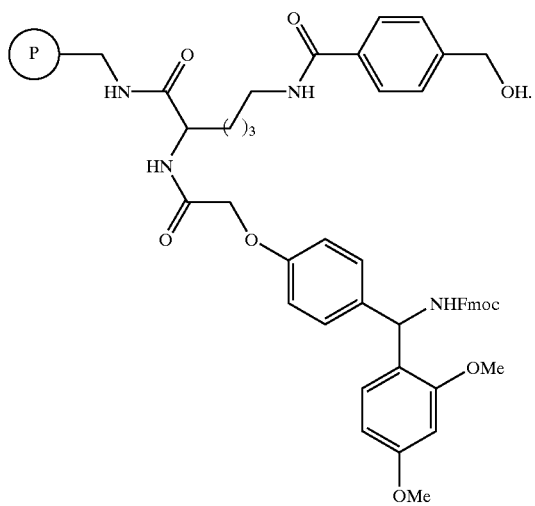

9. A multifinctionalized solid support resin having the structure

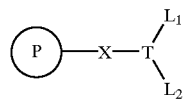

wherein P is a resin backbone, T is a template having at least three attachment points, X is a covalent bonding entity for attachment of T to P and $L_1$ and $L_2$ are independently selected from the group consisting of 4-hydroxymethylbenzoic acid (HMBA) and aminosulfonyl benzoic acid and when $L_1$ is HMBA, $L_2$ is aminosulfonyl benzoic acid and when $L_1$ is aminosulfonyl benzoic acid, $L_2$ is HMBA.

10. The multi-functionalized solid support resin of claim 9 having the structure:

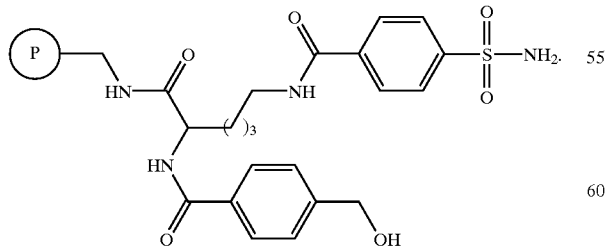

11. The multifunctionalized solid support resin of claim 3 having the structure:

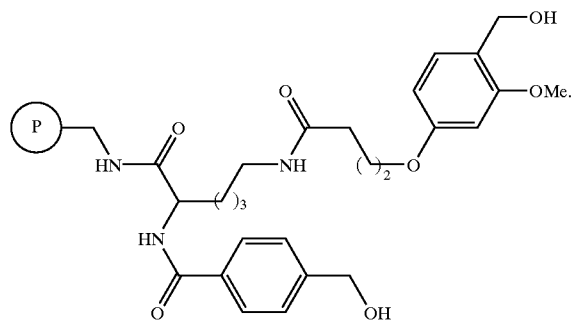

12. A multifunctionalized solid support resin having the structure:

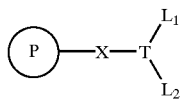

where P is a resin backbone, T is a diamino acid moiety having at least three attachment points, X is a covalent bonding entity for bonding T to P, $L_1$ and $L_2$ are structurally different benzyl linker moieties and are independently selected from the group consisting of acid-labile, base-labile, nucleophile-labile, electrophile-labile, photolabile, oxidant-labile and reductant-labile linkers having the formula:

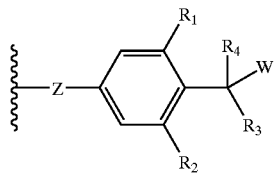

wherein Z is selected from the group consisting of a covalent bond, 0, —C(O)—, C1–6 alkylene, C5–10 aryl, carbonylC1–6alkylene, carbonylC1–6alkyleneoxy, carbonyl C5–10 aryl and carbonyl C5–10 heteroaryl, said alkylene, aryl and heteroaryl groups being substituted with H or C1–3 alkyl;

$R_1$ and $R_2$ are independently selected from the group consisting of H, nitro, halo and C1–6alkoxy;

$R_3$ and $R_4$ are independently selected from the group consisting of H, C1–6 alkyl, C5–10 aryl and C5–10 heteroaryl, said alkyl, aryl and heteroaryl groups being substituted; and W is selected from the group consisting of OH, $NH_2$ and NHpg where pg is a protecting group.

13. A method for preparing the multiftnctionalized support resin of claim 1, comprising:

a) coupling a diamino carboxylic acid template to a resin backbone, wherein each of the two amino groups of the diamino acid template are protected;

b) deprotecting one of the two protected amino groups of the template to generate a first deprotected amino group;

c) reacting the first deprotected amino group with a first benzyl linker moiety under conditions effective to covalently bond the benzyl linker moiety to the first deprotected amino group;

d) deprotecting the remaining protected amino group of the diamine carboxylic acid template to generate a second deprotected amino group;

e) reacting the second deprotected amino group with a second benzyl moiety under conditions effective to covalently bond the second benzyl linker moiety to the second deprotected amino group thereby to forming the multifunctionalized resin of claim 1; and f) recovering the multifunctionalized resin of claim 1.

* * * * *